(12) United States Patent  (10) Patent No.: US 7,584,534 B2
Pease et al.  (45) Date of Patent: Sep. 8, 2009

(54) REMOTE INSPECTION DEVICE

(75) Inventors: Alfred A. Pease, Ann Arbor, MI (US);
Al Boehnlein, Ypsilanti, MI (US); Tye Newman, Howell, MI (US); Paul J. Eckhoff, Fenton, MO (US)

(73) Assignee: Perceptron, Inc., Plymouth, MI (US)

( * ) Notice: Subject to any disclaimer, the term of this patent is extended or adjusted under 35 U.S.C. 154(b) by 417 days.

(21) Appl. No.: 11/480,329

(22) Filed: Jun. 30, 2006

(65) Prior Publication Data

US 2006/0281972 A1  Dec. 14, 2006

Related U.S. Application Data

(63) Continuation-in-part of application No. 11/328,603, filed on Jan. 10, 2006, which is a continuation-in-part of application No. 11/032,275, filed on Jan. 10, 2005, now abandoned.

(51) Int. Cl.
*B23P 19/00* (2006.01)
*H01R 43/00* (2006.01)
*H05K 13/04* (2006.01)

(52) U.S. Cl. ............... 29/729; 29/529.1; 29/593; 348/65; 348/74; 439/585; 439/587; 439/588; 439/589; 600/109; 600/129; 600/131; 600/175; 600/177

(58) Field of Classification Search ............... 29/592.1, 29/593, 729; 348/65, 74; 439/585, 587–589; 600/109, 129, 131, 175, 177, 179
See application file for complete search history.

(56) References Cited

U.S. PATENT DOCUMENTS

| 4,467,802 | A | 8/1984 | Maslanka |
| 4,471,766 | A | 9/1984 | Terayama |
| 4,778,247 | A | 10/1988 | Carpenter |
| 5,032,960 | A | 7/1991 | Katoh |
| 5,433,725 | A | 7/1995 | Christian et al. |
| 5,667,473 | A | 9/1997 | Finn et al. |
| 5,752,973 | A | 5/1998 | Kieturakis |
| 5,928,137 | A | 7/1999 | Green |

(Continued)

FOREIGN PATENT DOCUMENTS

EP  0587513  3/1994

(Continued)

*Primary Examiner*—Paul D Kim
(74) *Attorney, Agent, or Firm*—Harness, Dickey & Pierce, P.L.C.

(57) ABSTRACT

A remote inspection device is provided for inspecting visually obscured locations. The device is generally comprised of a imager housing and a display housing disposed on opposite ends of a modular, flexible cable. An imaging device is embedded in the end of the cylindrical imager housing, such that the imaging device is able to capture an image of a viewing area proximate to the distal end of the flexible cable. One or more light sources also protrude from the outwardly facing end of the cylindrical imager housing along a perimeter of the imaging device such that the imaging device is recessed between the light sources. A display housing is coupled to the other end of the flexible cable and configured to be grasped by a user of the device. A display device supported by the display housing receives a video signal from the imaging device and converts the video signal to a video image.

24 Claims, 13 Drawing Sheets

U.S. PATENT DOCUMENTS

| | | |
|---|---|---|
| 5,986,752 A | 11/1999 | Morito et al. |
| 6,086,528 A | 7/2000 | Adair |
| 6,091,453 A | 7/2000 | Coan et al. |
| 6,118,476 A | 9/2000 | Morito et al. |
| 6,221,007 B1 | 4/2001 | Green |
| 6,244,727 B1 | 6/2001 | Ryan, Jr. et al. |
| 6,320,182 B1 | 11/2001 | Hubble, III et al. |
| 6,369,849 B1 | 4/2002 | Rzyski |
| 6,402,347 B1 | 6/2002 | Maas et al. |
| 6,419,626 B1 | 7/2002 | Yoon |
| 6,577,339 B1 | 6/2003 | Thompson et al. |
| 6,692,432 B1 | 2/2004 | Yarush et al. |
| 6,767,110 B2 | 7/2004 | Cooper et al. |
| 6,796,939 B1 | 9/2004 | Hirata et al. |
| 7,009,698 B2 | 3/2006 | Drost et al. |
| 7,384,308 B2 * | 6/2008 | Boehnlein et al. ............ 439/585 |
| 7,431,619 B2 * | 10/2008 | Boehnlein et al. ............ 439/882 |
| 2001/0026315 A1 | 10/2001 | Ooshima et al. |
| 2002/0080615 A1 | 6/2002 | Marshall et al. |
| 2002/0139990 A1 | 10/2002 | Suehiro et al. |
| 2002/0163808 A1 | 11/2002 | West et al. |
| 2003/0035048 A1 | 2/2003 | Shipp |
| 2004/0054254 A1 | 3/2004 | Miyake |
| 2004/0193007 A1 | 9/2004 | Martone et al. |
| 2004/0199052 A1 | 10/2004 | Banik et al. |
| 2005/0129108 A1 | 6/2005 | Bendall et al. |
| 2006/0004258 A1 | 1/2006 | Sun et al. |
| 2006/0039160 A1 | 2/2006 | Cassarly et al. |
| 2006/0083000 A1 | 4/2006 | Yoon et al. |
| 2007/0225556 A1 | 9/2007 | Ortiz et al. |

FOREIGN PATENT DOCUMENTS

| | | |
|---|---|---|
| EP | 1212976 | 12/2002 |
| EP | 1860467 | 11/2007 |
| GB | 2407368 | 4/2005 |
| WO | WO99/50596 | 10/1999 |
| WO | WO0175359 | 10/2001 |
| WO | WO2005/073619 | 8/2005 |
| WO | WO2006/037034 | 4/2006 |
| WO | WO2006/073121 | 7/2006 |
| WO | WO2006/073122 | 7/2006 |
| WO | WO2006/073186 | 7/2006 |
| WO | WO2006/073187 | 7/2006 |
| WO | WO2006/075650 | 11/2007 |

* cited by examiner

REMOTE INSPECTION DEVICE

CROSS-REFERENCE TO RELATED APPLICATIONS

This application is a continuation-in-part of U.S. patent application Ser. No. 11/328,603 filed on Jan. 10, 2006, now pending which is in turn a continuation-in-part of U.S. patent application Ser. No. 11/032,275 filed on Jan. 10, 2005, now abandoned. The disclosures of the above applications are incorporated herein by reference.

FIELD

The present disclosure relates generally to borescopes and video scopes.

BACKGROUND

Borescopes and video scopes for inspecting visually obscured locations are typically tailored for particular applications. For instance, some borescopes have been tailored for use by plumbers to inspect pipes and drains. Likewise, other types of borescopes have been tailored for use by mechanics to inspect interior compartments of machinery being repaired. Special features and functions associated with these applications have driven up the cost for these types of devices. Absent from the marketplace is a simplified, inexpensive and yet versatile inspection device which may be marketed to the general public.

The statements in this section merely provide background information related to the present disclosure and may not constitute prior art.

SUMMARY

A remote inspection device is provided for inspecting visually obscured locations. The device is generally comprised of a imager housing and a display housing disposed on opposite ends of a flexible cable. An imaging device is embedded in an outwardly facing end of the cylindrical imager housing, such that the imaging device is able to capture an image of a viewing area proximate to the distal end of the flexible cable. One or more light sources also protrude from the outwardly facing end of the cylindrical imager housing along a perimeter of the imaging device such that the imaging device is recessed between the light sources. A display housing is coupled to the other end of the flexible cable and configured to be grasped by a user of the device. A display device supported by the display housing receives a video signal from the imaging device and converts the video signal to a video image.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
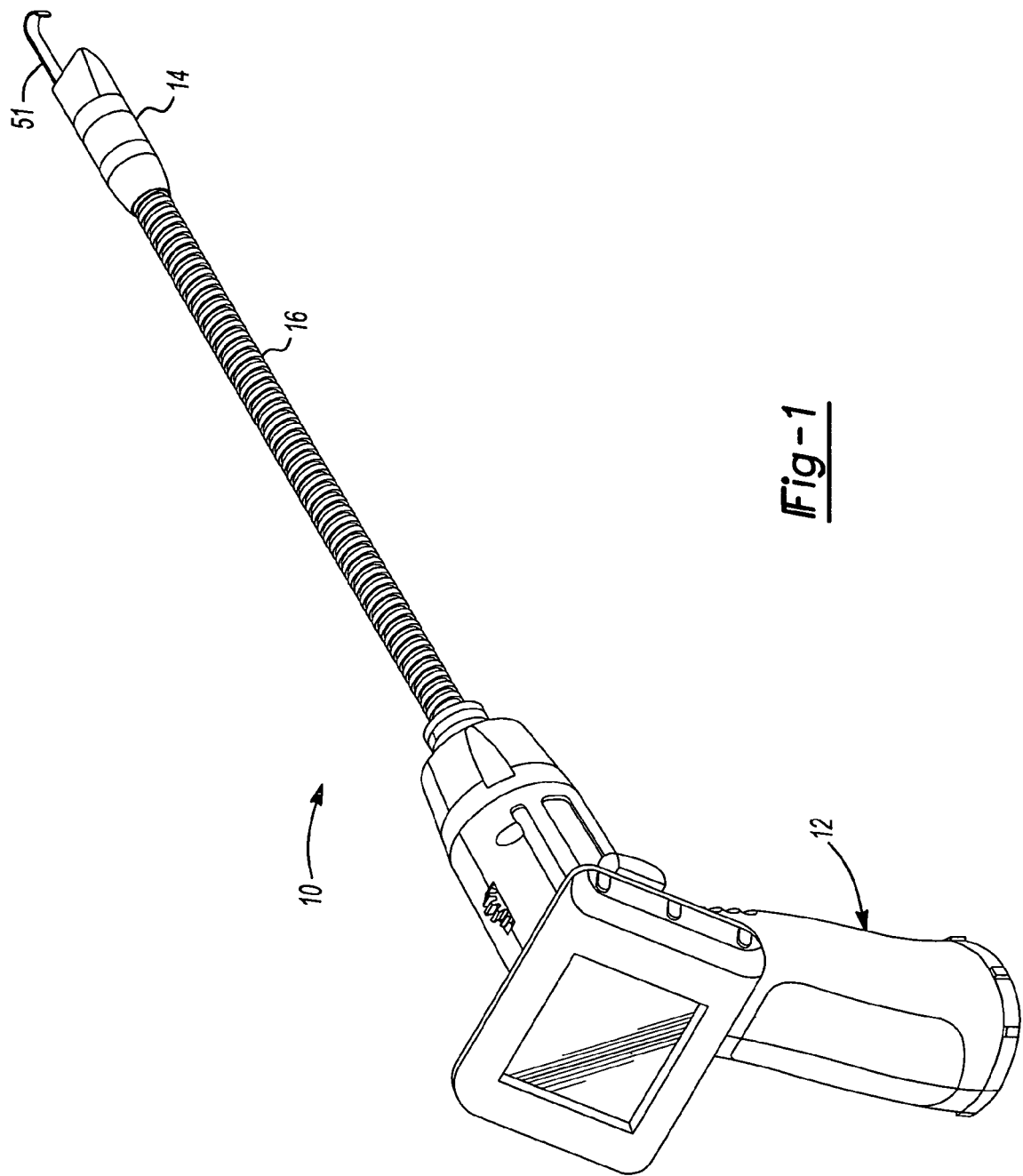
FIG. 1 is a perspective view of an exemplary inspection device.

FIG. 1 illustrates an exemplary embodiment of a remote inspection device 10. The remote inspection device 10 is generally comprised of three primary components: a display housing 12, an imager housing 14 and a flexible cable 16 interconnecting the display housing 12 to the imager housing 14. The flexible cable 16 may be bent or curved as it is pushed into visually obscured areas, such as pipes, walls, etc. In an exemplary embodiment, the flexible cable 16 is a ribbed cylindrical conduit having an outer diameter in the range of 1 cm. The conduit can be made of either a metal, plastic or composite material. Smaller or larger diameters may be suitable depending on the application. Likewise, other suitable constructions for the flexible cable 16 are also contemplated by this disclosure.

The imager housing 14 is coupled to a distal end of the flexible cable 16. In the exemplary embodiment, the imager housing 14 is a substantially cylindrical shape that is concentrically aligned with the flexible cable 16. However, it is envisioned that the imager housing 14 may take other shapes. In any case, an outer diameter of the cylindrical imager housing 14 is preferably sized to be substantially equal to or less than the outer diameter of the flexible cable 16.

Figure 2A:
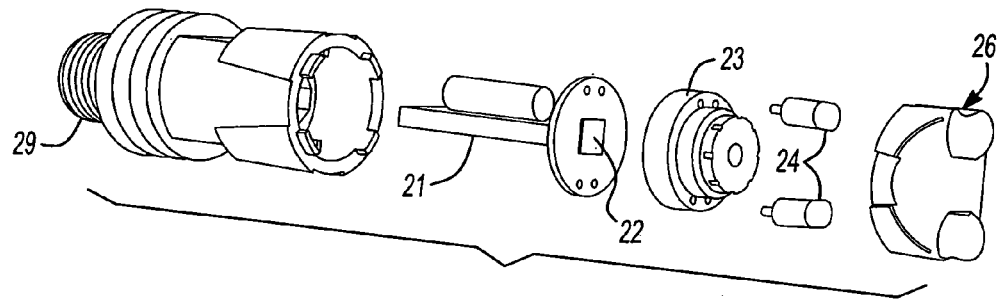
FIGS. 2A and 2B are exploded views of exemplary imager housings of the inspection device.

With reference to FIG. 2A, the imager housing 14 is configured to house an imaging device 22 and one or more light sources 24. The imaging device 22 is embedded in an outwardly facing end of the imager housing. In particular, the imaging device 22 is coupled to an end of a circuit board 21 which in turn slides into an internal cavity of the imager housing 14. The imaging device 22 is operable to capture an image of a viewing area proximate to the outwardly facing end of the imager housing 14. The imaging device 22 may be implemented using a charge-coupled device (CCD), a CMOS-based image sensor, a digital image sensor, or other types of commercially available imaging devices. Image data is focused onto the imaging device 22 by a lens assembly 23 positioned adjacent to the imaging device 22.

Figure 3:
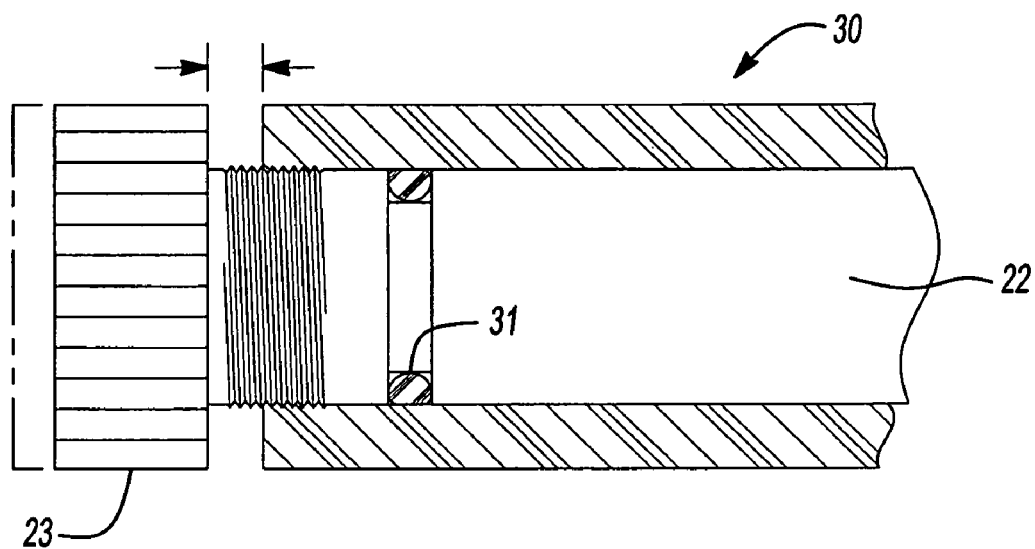
FIG. 3 is a cross-sectional view of a imager housing having a sealable user adjustable focus mechanism.

In the exemplary embodiment, the imaging device 22 and lens assembly 23 provides a fixed focus at approximately four to ten inches from the end of the imager housing. However, it is envisioned that the inspection device 10 may provide an adjustable focus. For instance, a user adjusted focus mechanism 30 is shown in FIG. 3. Through a fine mechanical screw thread or any similar movement device, the lens assembly 23 can be moved axially nearer or farther from the imager 22. This movement changes the focus of the imaging device. At the same time, a seal 31 must be provided to prevent foreign materials from entering the mechanism. In another instance, the imaging device and lens assembly may be replaced with an auto-focus camera module. In this instance, a more sophisticated processor and drive motor assembly is needed to drive the camera module.

Figure 2B:
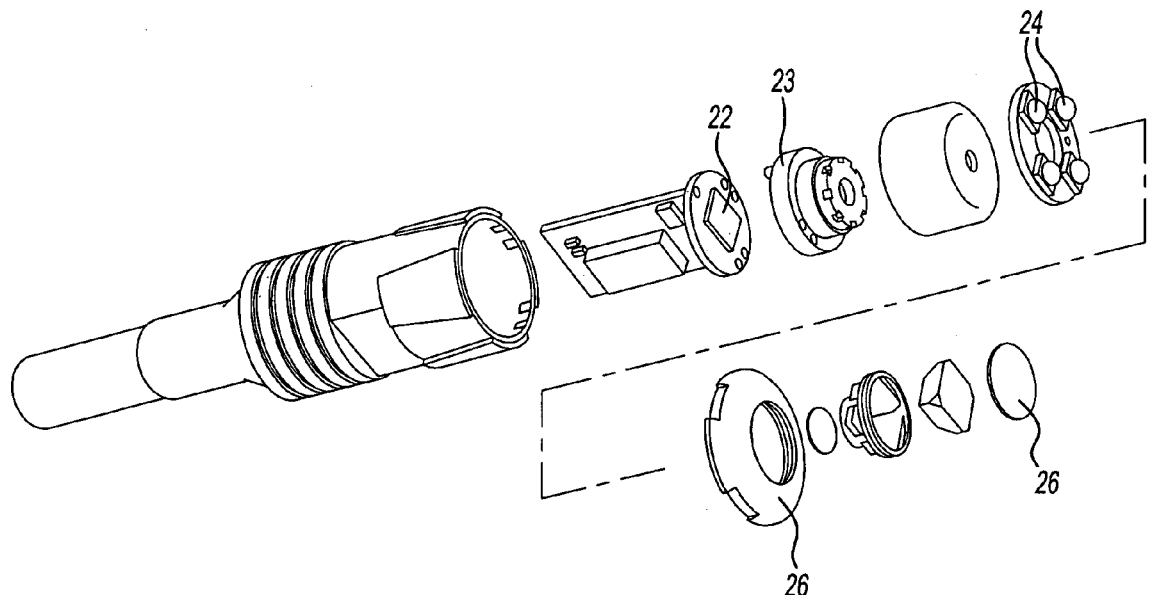
Figure 2C:
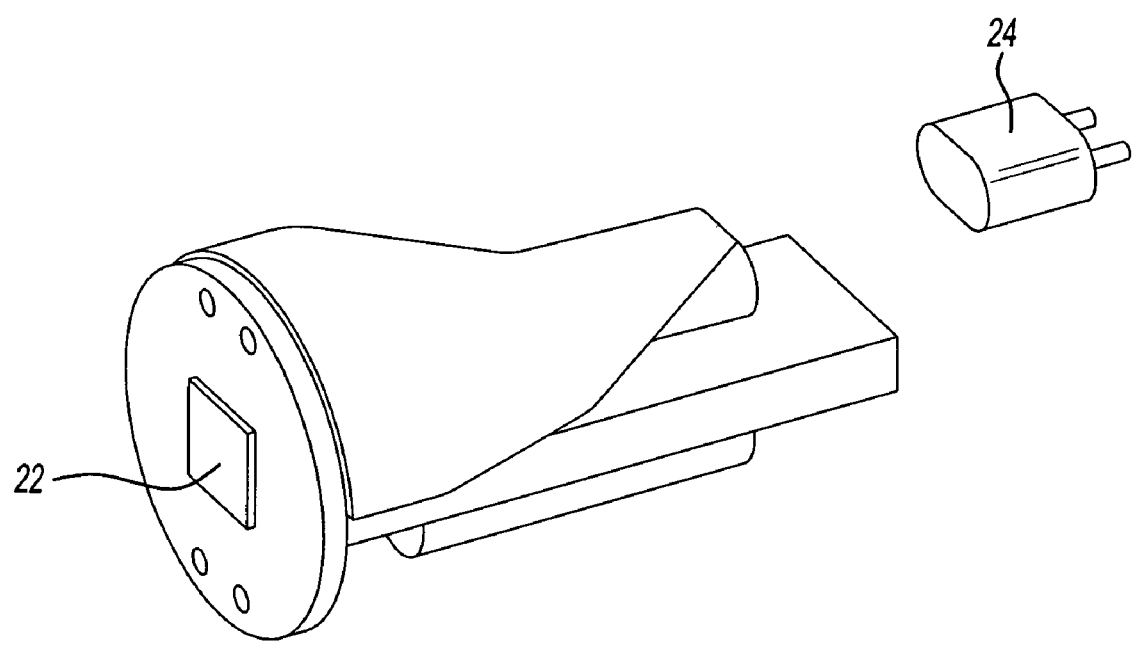
FIG. 2C is a diagram depicting an exemplary piping structure for guiding light through the imager housing.
Figure 4:
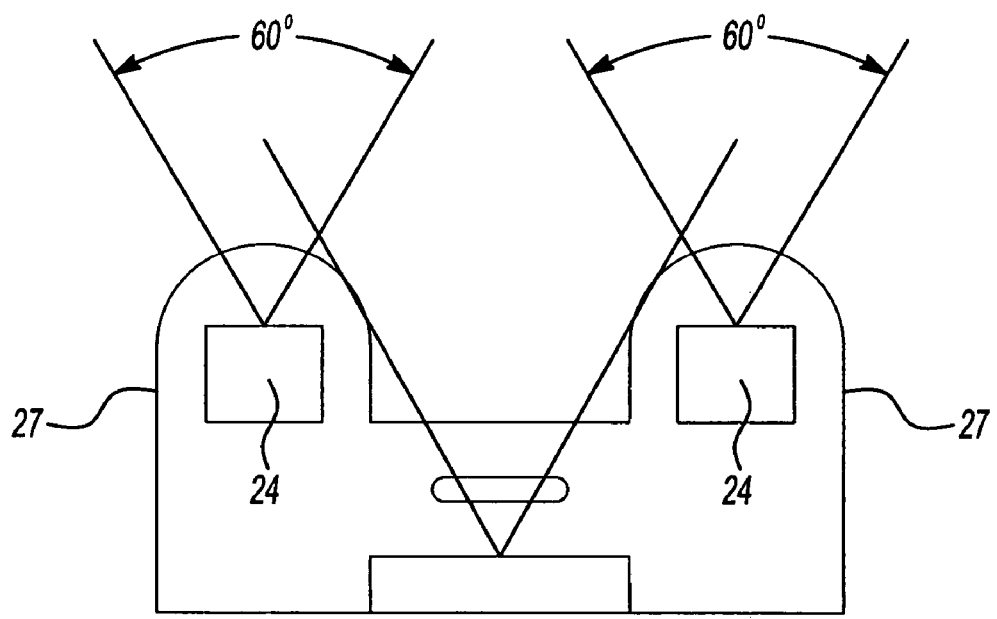
FIG. 4 is a cross-sectional schematic view of the imager housing.

With continued reference to FIG. 2A, one or more light sources 24 for illuminating the viewing area are also electrically connected to the circuit board 21. In the exemplary embodiment, two light emitting diodes (LEDs) are disposed along the perimeter of the imaging device 22. The LEDs protrude outwardly from the circuit board such that the imaging device 22 and lens assembly 23 is recessed between the two LEDs as shown in FIG. 4. The LEDs may optionally be connected to a separate circuit board residing in the camera head. Alternatively, the LEDs 24 may be recessed behind the imaging device 22 and/or lens assembly, such that light from the LEDs is transferred or piped to an emitting point which extends above and beyond the imaging device 22. An exemplary piping structure is shown in FIG. 2C. In either instance, recessing the imaging device and lens assembly behind the light emitting point reduces the amount of backscattered or interfering light from the LEDs.

A transparent cap 26 encloses these components within the imager housing 14. For instance, the cap 26 may be made of an acrylic material that enables light to project from the LEDs into the viewing area and return from the viewing area to the imaging device. Other types of durable transparent material may be used in place of acrylic. In the exemplary embodiment, each of the protruding LEDs is encased by a nipple 27 formed in the cap 26. To sufficiently illuminate the viewing area, each LED should preferably project light proximate to the view angle of the imager at a 60 degree view angle away from the image housing 14. LEDs having such a view angle may be used. However, LED's having a 132 degree view angle provide a more inexpensive alternative. In this case, the ends of the nipples 27 may be curved to form a lens which focuses the light from the LEDs to a 60 degree view angle as shown in FIG. 4. Thus, the cap 26 may also serve as a lens for the light sources. The cap 26 is preferably ultrasonically welded to the outwardly facing end of the imager housing 14, thereby creating a sealed enclosure; otherwise, techniques for sealing the cap to the imager housing are also contemplated. An alternative embodiment for the imager housing 14 is shown in. FIG. 2B.

In one exemplary embodiment, the imager housing 14 couples to the flexible cable 16 by way of a threaded sleeve 29 integrally formed at one end of the imager housing 14. The threaded sleeve 29 on the imager housing screws into a grooved portion from along an interior surface of a coupling formed on the distal end of the flexible cable. The sleeve and coupling each provide an axial passageway for a plurality of wires that are electrically connected between the circuit board in the imager housing and the display housing. The plurality of wires may or may not be further encased in a protective cable.

Figure 5A:
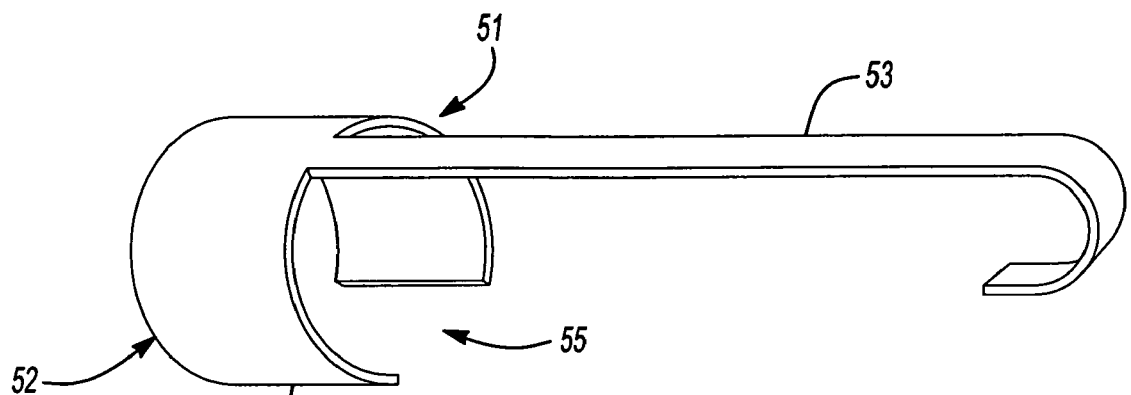
FIGS. 5A-5C are perspective views of exemplary attachments for the imager housing.
Figure 5B:
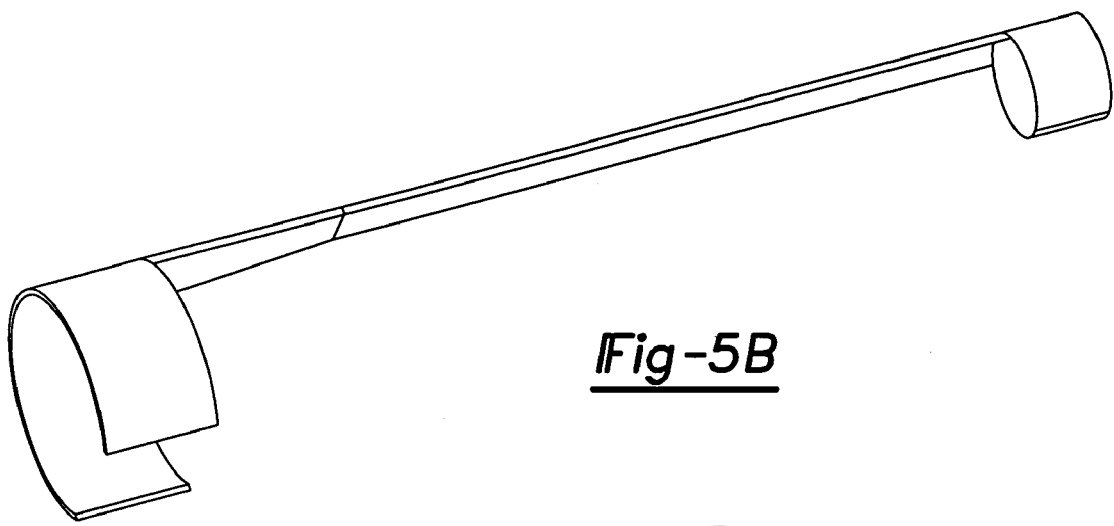
Figure 5C:
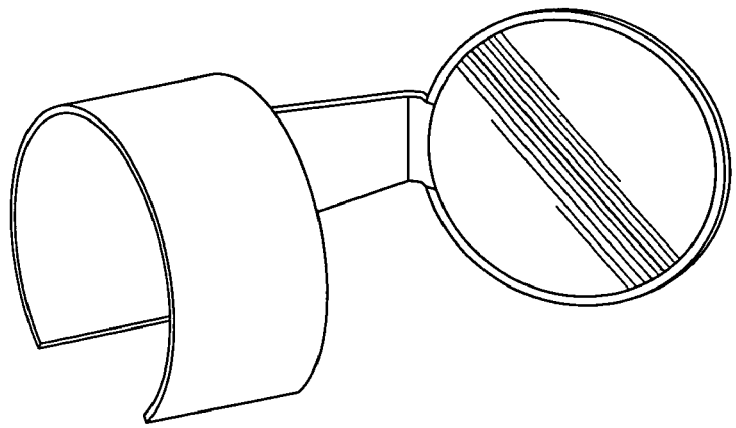

With reference to FIGS. 5A-5C, an attachment 51 may be removably coupled to the imager housing 14. The attachment 51 is generally comprised of a finger portion 53 which extends in parallel to the axis of the cylindrical imager housing and beyond an outwardly facing end of the housing, and a clip 52 that attaches to the cylindrical housing. A distal end of the finger portion 53 may be further configured to retrieve or otherwise manipulate objects proximate to the end of the imager housing 14. For instance, the attachment 51 may be configured with a hook as shown in FIG. 5A or with a magnet as shown in FIG. 5B. In another instance, the attachment may be a mirror as shown in FIG. 5C. Other configurations, such as a loop, lance, or cutting device, are also contemplated by this disclosure.

Figure 6A:
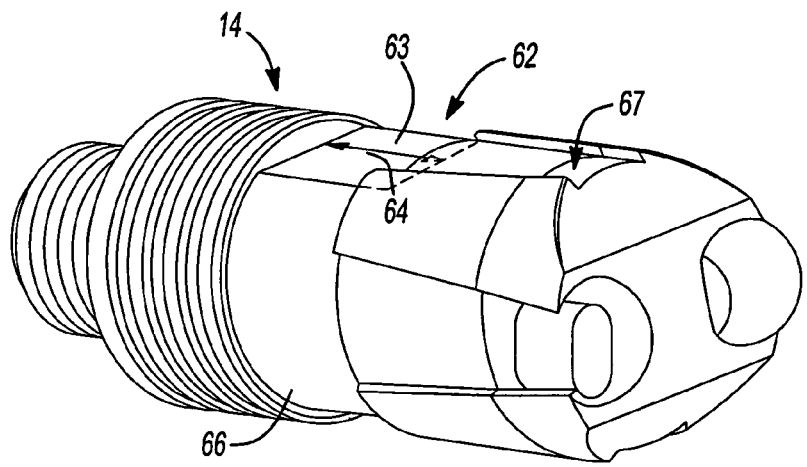
FIG. 6A is a perspective view illustrating the engagement area for an exemplary attachment on the imager housing.

In an exemplary embodiment, the imager housing provides an engagement area for the attachment 51 as shown in FIG. 6A. The engagement area is comprised of an annular recess 62 formed in the outer surface of the imager housing. Within the annular recess, two opposing cutaways 62 are also formed, where each cutaway 62 defines a recessed rectangular planar surface 63 having a longitudinal axis 64 in parallel with the axis of the cylindrical imager housing. A radial surface 66 is formed between the two opposing cutaways. The clip 52 is further defined as a cylindrical band 54 having a radial gap 55 formed therein, such that the radial gap 55 of the clip 52 is slightly larger than the remaining radial surface 66. In addition, the annular recess 62 is sized to receive the cylindrical band 54 of the clip. The engagement area may further include a locking groove 67 formed in the radial surface thereof and extends in parallel to the axis of the cylindrical imager housing. The locking groove 67 is sized to receive the finger portion 53 of the attachment.

Figure 6B:
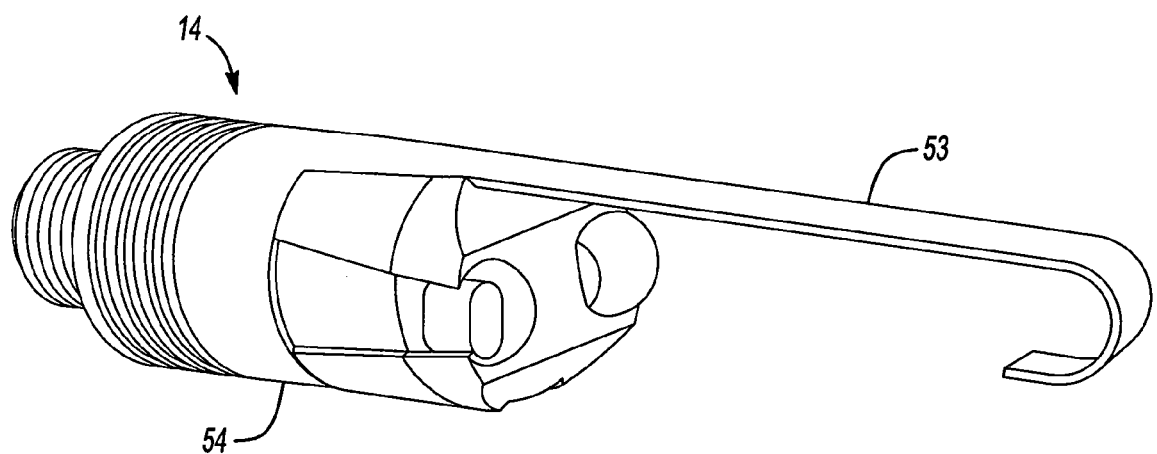
FIG. 6B is a perspective view illustrating an exemplary attachment coupled to the imager housing.
Figure 6C:
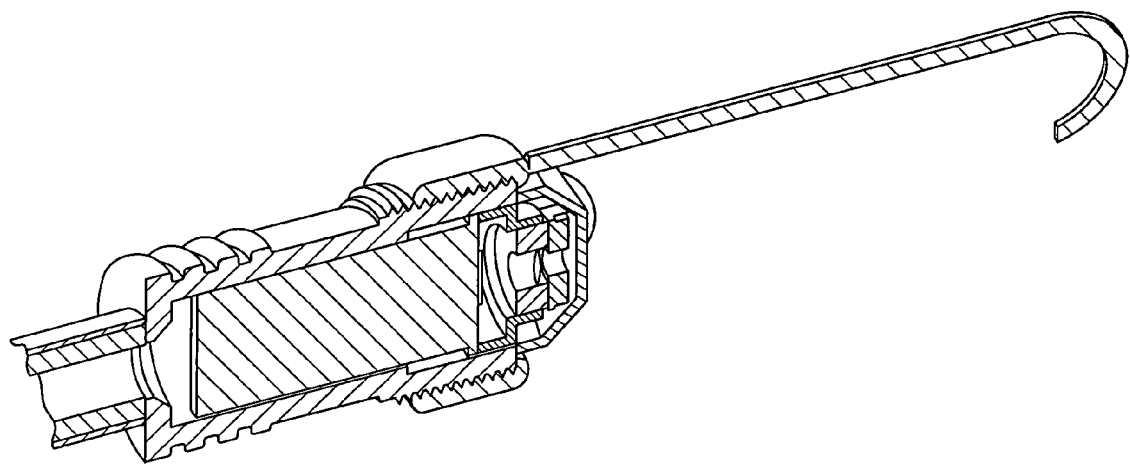
FIG. 6C is a perspective view illustrating an alternative coupling means for attaching an attachment to the imager housing.

Referring to FIG. 6B, the attachment 51 is coupled to the imager housing 14 by sliding the cylindrical band 54 over the recessed portion of the housing 14 and into the annular recess 62. Recessed into the annular recess prevent the attachment from sliding forward or backwards along the imaging housing. The attachment 51 is then rotated 90 degrees around the axis of the housing until the finger portion 53 of the attachment 51 is recessed into the locking groove, thereby preventing attachment 51 from rotating about. The spring load of the band pulls the finger portion into the locking groove 67 to further prevent detachment from the imager housing. It is understood that the clip mechanism is a non-limiting example of how the attachment may be removably coupled to the imager housing. FIG. 6C illustrates a threaded coupling between the attachment 51 and the imager housing 14. Other coupling means, such as magnetic, are also contemplate by this disclosure.

Figure 7:
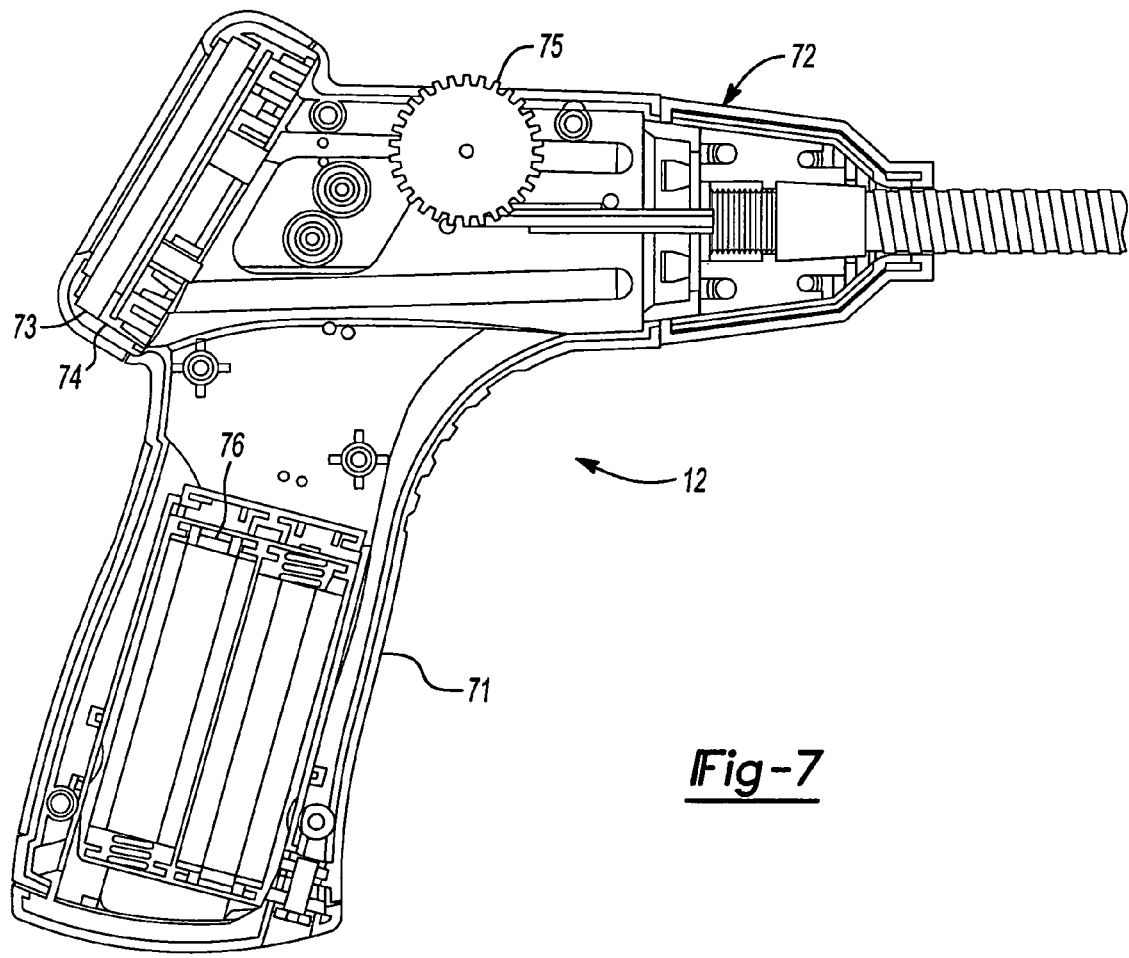
FIG. 7 is a cross-sectional view of an exemplary display housing.

Referring to FIG. 7, the display housing 12 is coupled to a proximate end of the flexible cable 16. In an exemplary embodiment, the display housing 12 is in the shape of a pistol. Specifically, the display housing 12 includes a handle portion 71 configured to be grasped by an operator of the device and a protruding portion 72 extending away from the user when grasped by the user, such that the protruding portion forms an obtuse angle relative to the handle portion of the housing display. Other handheld configurations for the display housing also fall within the broader aspects of this disclosure.

Figure 8A:
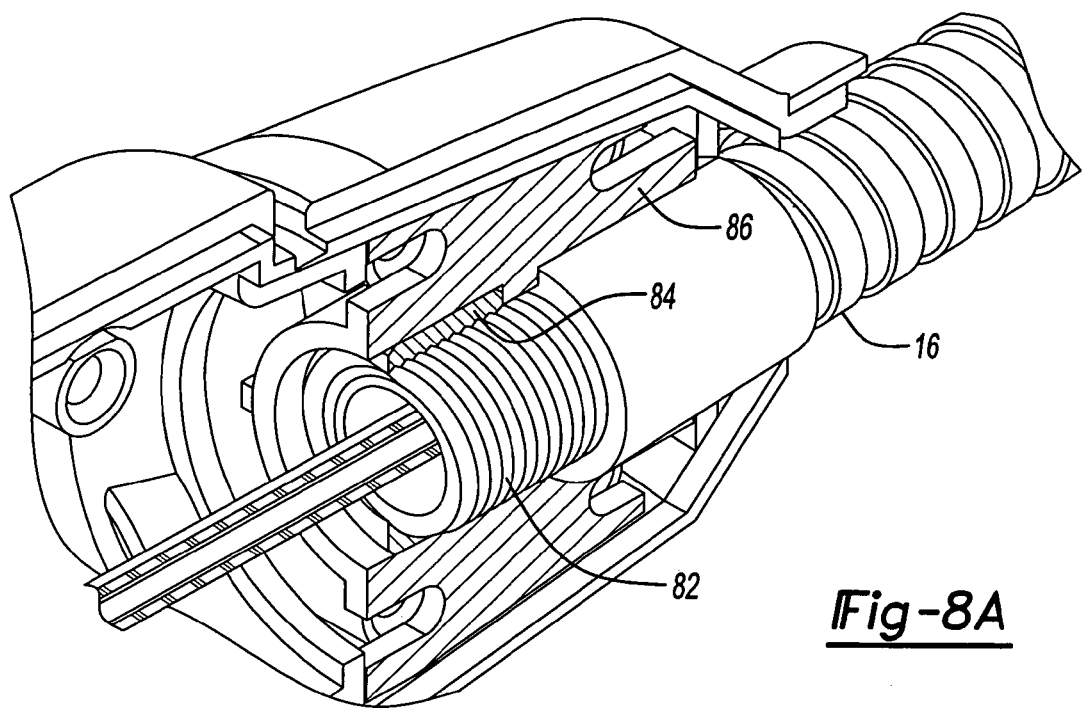
FIGS. 8A and 8B are fragmentary sectional views illustrating the coupling of the flexible cable to the display housing.
Figure 8B:
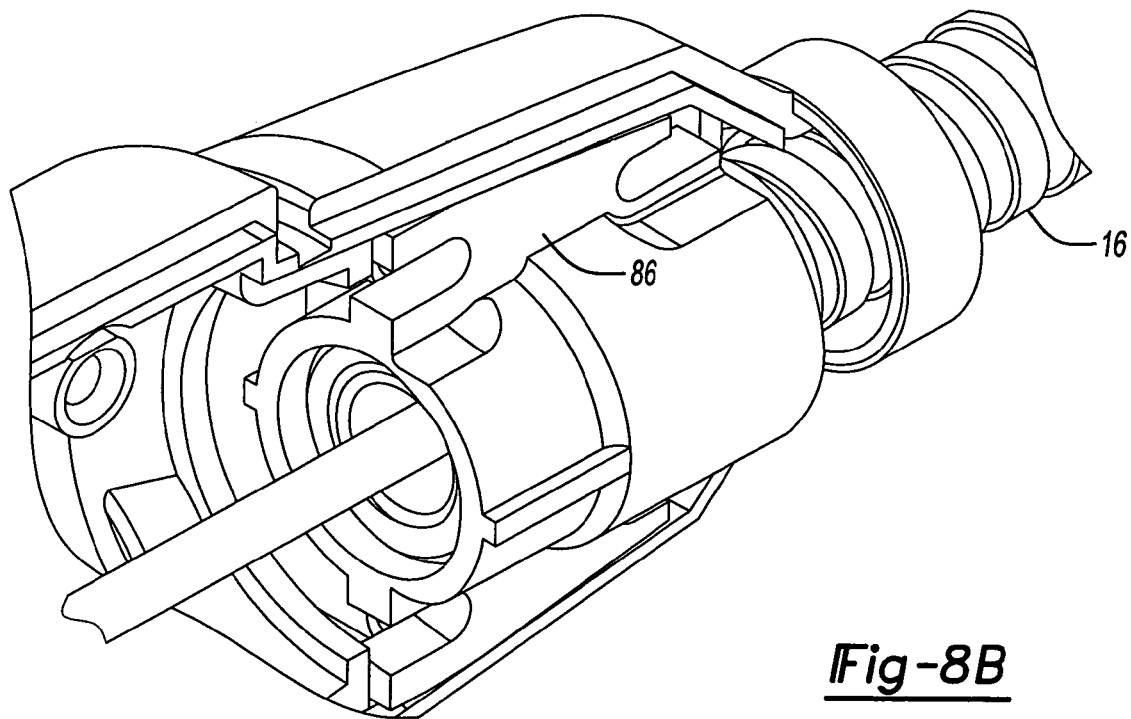

In one exemplary embodiment, a threaded male connector 82 formed on the proximate end of the flexible cable 16 is used to couple the cable to the display housing 12 as best seen in FIGS. 8A and 8B. In this case, a knurled nut 84 is fixed with the nut retainer 86. The male connector 82 is screwed into the knurled nut 84, thereby coupling the flexible cable 16 to the nut retainer 86. The nut retainer is then attached into the protruding portion of the display housing 12. Other types of connections are contemplated by this disclosure.

Returning to FIG. 7, the display housing 12 is configured to support the remaining operational components of the inspection device. In the exemplary embodiment, the operational components include a display device 73, an interface board 74, a power switch 75 and a power source 76 (i.e., 4 AA alkaline batteries). The display device 73 is preferably orientated towards the operator as the operator grasps the handle portion 71 of the device. Although a liquid crystal display is presently preferred, it is understood that other types of display devices, such a cathode ray tube or a LED display, may also be used.

Figure 9:
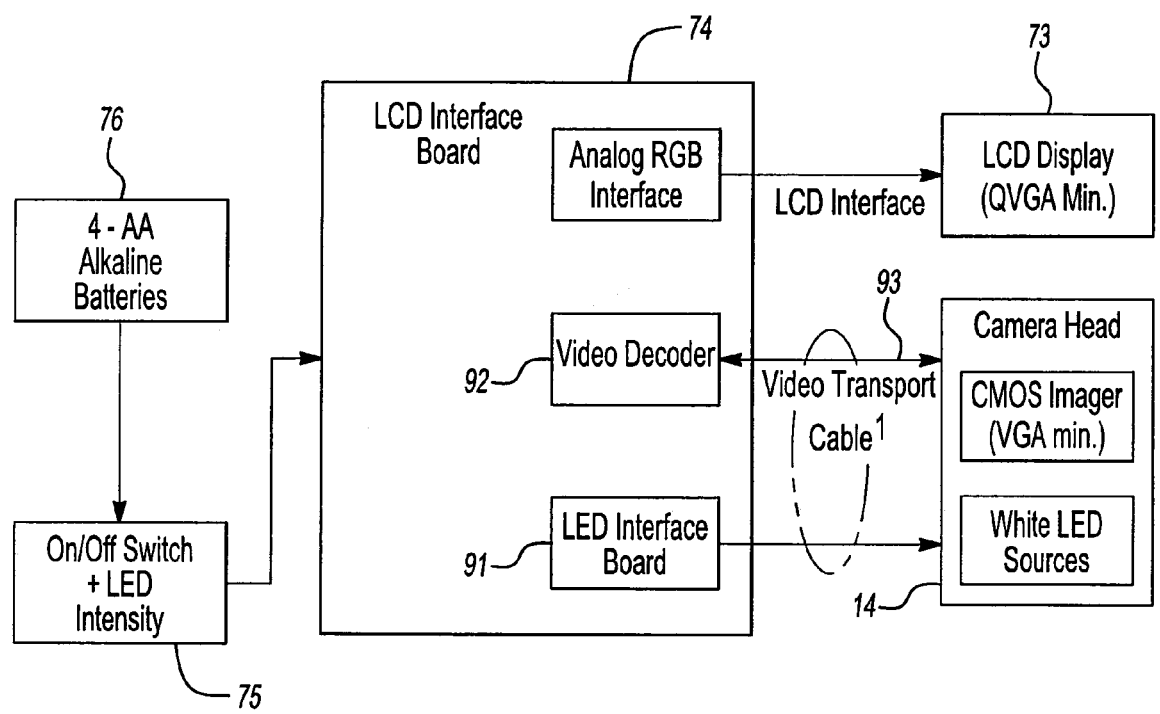
FIG. 9 is a block diagram of the operational components which comprise the inspection device.

Operational aspects of the inspection device are better understood from a schematic provided in FIG. 9. The power switch 75 is interposed between the power source 76 and the remaining operational components. When actuated by an operator to an ON position, power is supplied from the power source 76 to the interface board 74. The interface board 74 in turn powers the display device 73 and the imaging device 22.

In the exemplary embodiment, the power switch 75 is further operable to control the intensity of the LEDs. To do so, power is also supplied to an LED interface board 91. The LED interface board 91 in turn sends a control signal to the LEDs based on the setting of the power switch 75. As the dial is rotated further away from an ON position, the intensity of the LEDs is increased. In this way, the operator can adjust the illumination of the viewing area, thereby improving the quality of the acquired images. Alternative embodiments of the inspection device may employ other user actuated controls. For example, the inspection device may include controls for the contrast of the display device, on-screen display or for a zoom function of the imaging device.

Once powered on, the imaging device 22 begins capturing images and transmitting the image data as a video signal to a video decoder 92 residing on the interface board 74. The video decoder 92 decodes the video signal and passes it through another interface to the display device 73. The display device 73 is then operable to display the video images to the operator.

In the exemplary embodiment, the imager housing is connected by a four wire twisted pair cable to the display housing. Functions for each wire are specified as follows: a power wire for delivering electrical power to the imaging device, a video wire for transporting the captured image data (e.g., a NTSC signal) from the imager back to the interface board, a control signal for varying the intensity of the light source and a ground connection. It is envisioned that more or less wires may be needed to support different functionality.

In an alternative embodiment, the inspection device may provide an image self-righting feature. As the camera head is pushed into inspection areas, it may get twisted so that the images displayed to the operator are disoriented. To orientate the images, an accelerometer is placed in the imager housing. The accelerometer is operable to report the position of the camera head in relation to a sensed gravity vector. Given the position data and the image data, a microprocessor residing in the display housing can apply a known rotation algorithm (e.g., rotation matrix) to the image data. In this way, the image data is always presented upright to the operator.

Figure 10:
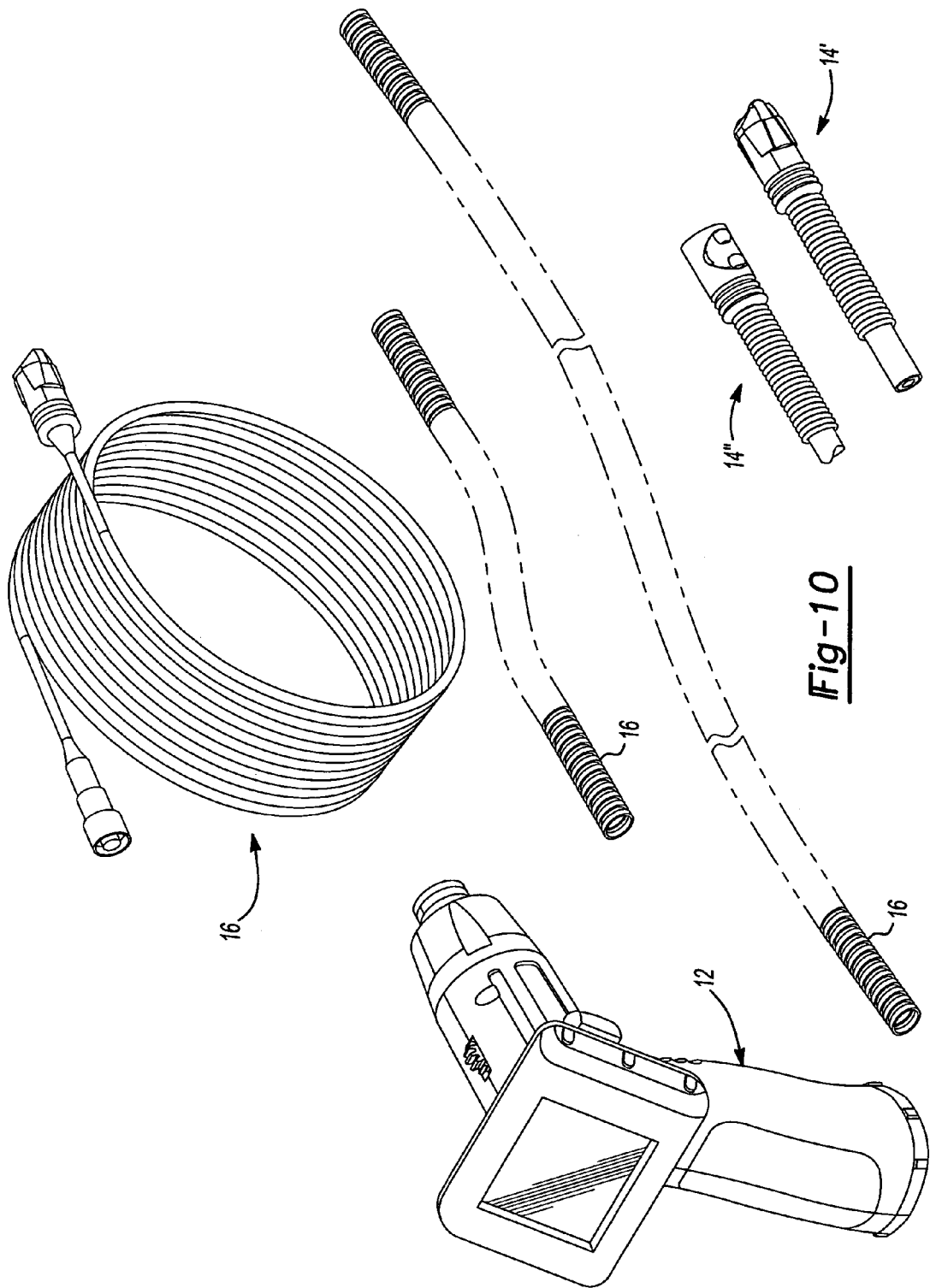
FIG. 10 is a perspective view illustrating a modular design for the inspection device.

In another aspect of this disclosure, the remote inspection device may be designed to be modular as shown in FIG. 10. In general, the more expensive processing components, such that the LCD, are disposed in the display housing; whereas, lesser expensive components are used to construct the imager housing. Modularity enables the lesser expensive components to be interchanged or replaced as needed.

For example, a detachable coupling between the imager housing and the flexible cable enables imager housings of varying sizes to be used with the same display housing. The flexibility allowed by the modularity of this device also allows the cost efficient manufacture of easily replaceable imager heads that could be fixed at any desired spherical orientation in regard to the central axis of the cable or the imager head. A first imager head 14' may be constructed as described above with the imaging device orientated along the central axis of the imager head; whereas, a second imager head 14" provides an imaging device orientated at 90 degrees to the central axis of the imager head. Imager heads have other orientations are also contemplated.

Likewise, a second detachable coupling between the display housing and the flexible cable enables the use of different types of cables while retaining the same imager housing. Depending on the application, cables may vary in length from 3 feet to more than 50 feet and may vary in diameter from less than an inch to a couple of inches in diameter. Moreover, different cables may have different flexibilities, stiffnesses, spring tensions, obedient cable properties, tape measure material similarities, fish-tape or fish-stick similarities, push-cable similarities, etc. It is envisioned that the remote inspections device may be sold as a kit having a display housing 12, at least one imager head 14 and a set of different cables having different constructs. Additional imager heads may be included in the kit or sold individually.

Given an adaptable display housing, users may configure the inspection device to meet their particular needs. For a first task, a first type of cable attachment along with a particular image head may be selected and coupled to the display housing. For a different task, the user may detach the image head and attach an image head which provides a different function. Alternatively, the user may also need to replace the cable attachment. In this case, the user further detaches the first type of cable attachment and attaches a second type of cable attachment having a different construct than the first type of cable attachment. For example, the second type of cable attachment may have a different length, diameter, or flexibility than the first type of cable attachment. The user then selects and attaches a suitable image head to the second type of cable attachment. In this way, the more expensive display housing may be configured with different and less expensive components tailored to a particular task.

Figure 11A:
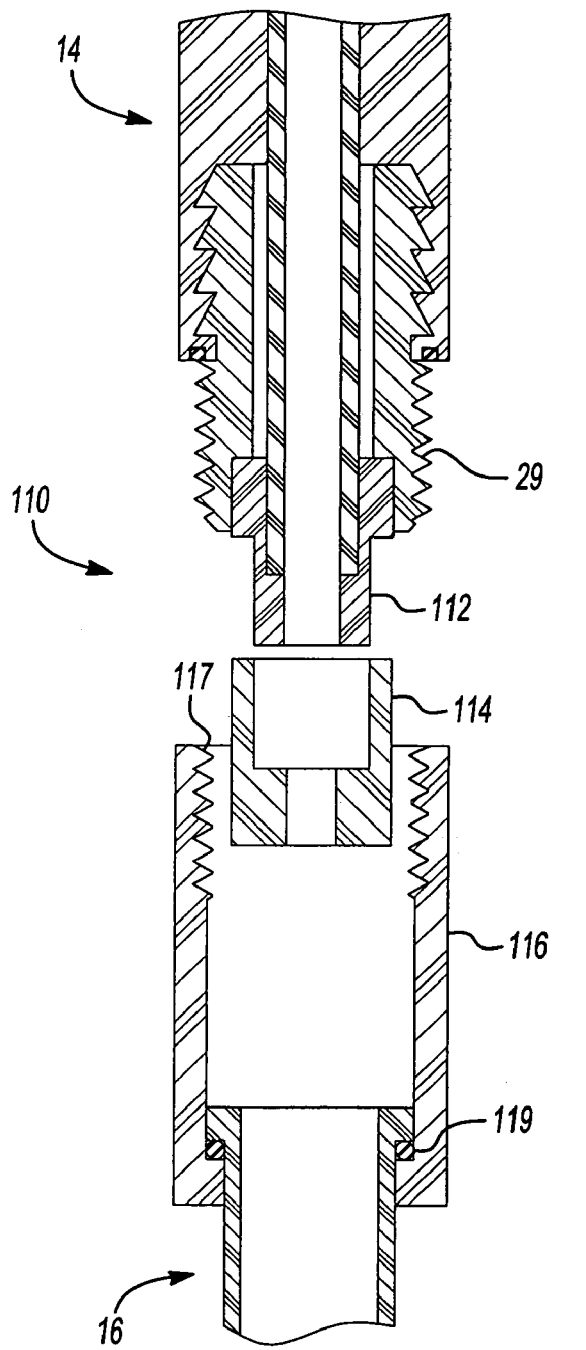
FIGS. 11A and 11B are cross-sectional view of a detachable coupling which may be used in the inspection device.
Figure 11B:
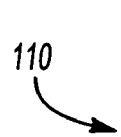

FIGS. 11A and 11B illustrate an exemplary detachable coupling 110 which may be interposed between the imager housing 14 and the flexible cable 16. On the camera side, a cylindrical sleeve 29 having an outer threaded portion protrudes from the housing. A male connector 112 is fixed within an axial passageway of the threaded sleeve. The male connector 112 is in turn electrically connected via the applicable wires to the imaging device and light sources. On the other hand, a corresponding female connector 114 is coupled to the distal end of the flexible cable 16. Likewise, the female connector 114 is electrically connected to wires which extend through the flexible cable 16 to the display housing. By plugging the male connector 112 into the female connector 114, the imager housing 14 is electrically connected to the flexible cable 16.

To provide a sealed coupling, a cylindrical coupling 116 is also disposed on the distal end of the flexible cable 16. The cylindrical coupling 116 further provides an internal grooved portion 117 which mates with the threaded portion of the sleeve on the imager housing. To complete the coupling, the cylindrical coupling 116 is slid over the female connector and screwed onto the threaded portion of the sleeve, thereby encasing the electrical connection within the coupling. An O-ring 119 or other sealing component is preferably disposed between the inner surface of the cylindrical coupling and the outer surface of the flexible cable. A detachable coupling having a similar construction may be interposed between flexible cable and the display housing. Moreover, it is envisioned that other types of detachable couplings may be employed to achieve the modularity.

Figure 12:
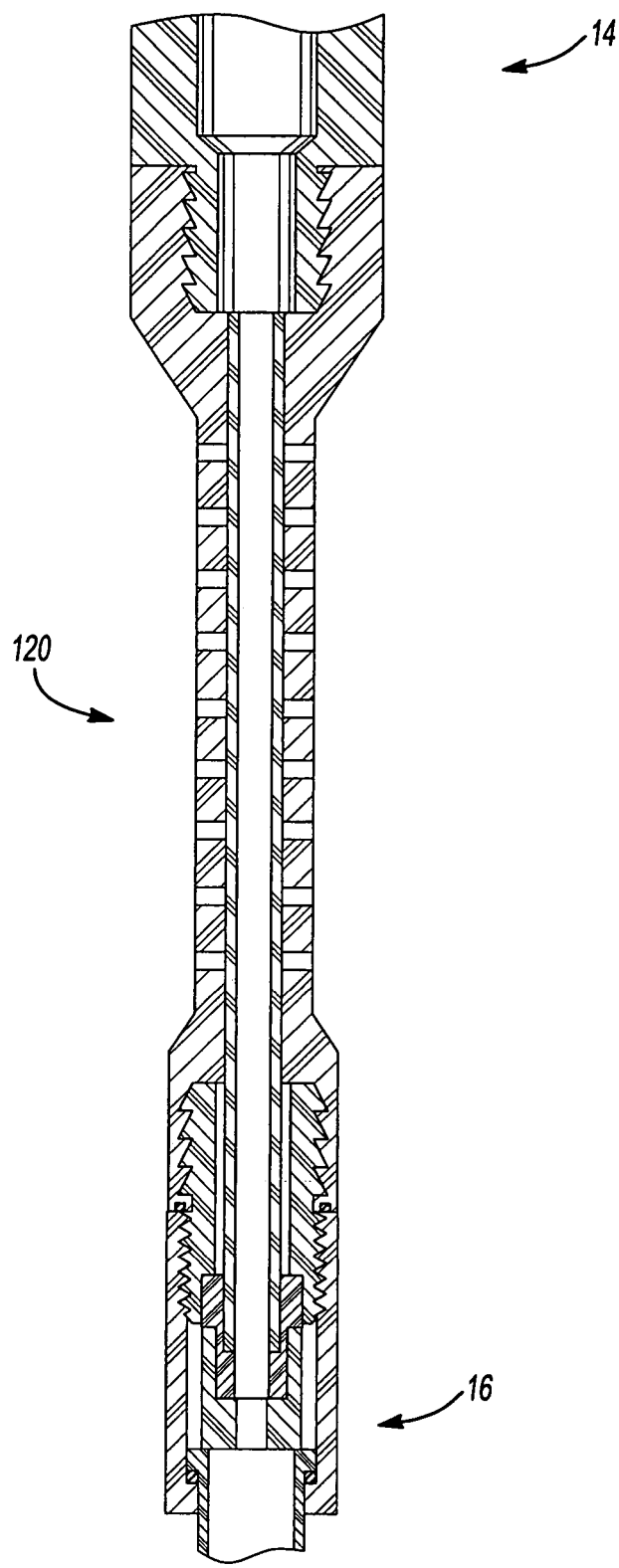
FIG. 12 is a cross-sectional view of a secondary connector which may be used with the inspection device.

In an alternative embodiment, a secondary connector 120 may be interposed between the imager housing 14 and the flexible cable 16 as shown in FIG. 12. The secondary connector 120 is designed to be more flexible than the flexible cable, thereby providing strain relief as the imager housing is snaked into an inspection area. In the exemplary embodiment, a corrugated outer surface of the secondary connector 120 provides its flexibility. On the camera side, a cylindrical sleeve having an outer threaded portion protrudes from the housing. In an exemplary embodiment, one end of the secondary connector 120 is overmolded around the cylindrical sleeve to form a coupling between the image housing 14 and the secondary connector. The other side of the secondary connector can be constructed in manner described above for coupling to the flexible cable. Again, this type of secondary connector may also be interposed between the other end of the flexible cable and the display housing.

The following description is merely exemplary in nature and is not intended to limit the present disclosure, application, or uses.

What is claimed is:

1. A remote inspection device, comprising:
   a flexible cable having a proximate end and a distal end;
   a substantially cylindrical imager housing concentrically aligned with and coupled to a distal end of the flexible cable;
   an imaging device embedded in an outwardly facing end of the cylindrical imager housing, the imaging device operable to capture an image of a viewing area proximate to the distal end of the flexible cable and convert the image into a video signal;
   one or more light sources protruding from the outwardly facing end of the cylindrical imager housing along a perimeter of the imaging device such that the imaging device is recessed between the at least one light sources;
   a transparent cap that encases the imaging device and light sources within the imager housing, wherein each of the at least one light sources protrudes into a nipple formed in the cap and the nipple is shaped to focus light from each of the at least one light sources into the viewing area; and
   a display housing coupled to the proximate end of the flexible cable and configured to be grasped by a user of the device, where the display housing includes a display device adapted to receive the video signal from the imaging device and operable to convert the video signal to a video image.

2. The remote inspection device of claim 1 wherein the at least one light sources are further defined as light emitting diodes.

3. The remote inspection device of claim 1 wherein the cap is made of a transparent plastic.

4. The remote inspection device of claim 1 wherein the cap is ultrasonic welded to the imager housing.

5. The remote inspection device of claim 1 wherein the housing display having a shape of a pistol.

6. The remote inspection device of claim 1 wherein the housing display having a handle portion configured to be grasped by a user of the device and a protruding portion extending away from the user when grasped by the user, such that the protruding portion form an obtuse angle relative to the handle portion of the housing display.

7. The remote inspection device of claim 1 wherein the flexible cable is constructed from a cylindrical conduit.

8. The remote inspection device of claim 1 wherein the display device is further defined as a liquid crystal display.

9. The remote inspection device of claim 1 further comprises an attachment that removably couples to the cylindrical imager housing, the attachment having a finger portion which extends in parallel to the axis of the cylindrical imager housing and beyond an outwardly facing end of the housing.

10. The remote inspection device of claim 9 wherein the attachment further includes a clip that attaches to the cylindrical housing.

11. The remote inspection device of claim 10 wherein the cylindrical imager housing provides an annular recess sized to receive the clip of the attachment.

12. The remote inspection device of claim 11 wherein the cylindrical imager housing includes two opposing cutaways formed in the annular recess of the imager housing and a radial surface interposed between each of the opposing cutaways, and the clip of the attachment is further defined as a cylindrical band having a radial gap formed therein, where the radial gap is larger than the radial surface of the imager housing.

13. The remote inspection device of claim 12 wherein the cylindrical imager housing further includes a locking groove formed in the radial surface thereof and extends in parallel to the axis of the cylindrical imager housing, where the locking groove is sized to receive the finger portion of the attachment.

14. The remote inspection device of claim 1 further includes an accelerometer disposed in the imager housing and operable to report orientation of the imager housing in relation of a gravity vector, and a microprocessor disposed in the display housing, wherein the microprocessor is adapted to receive the video signal from the imaging device and the orientation data from the accelerometer and operable to orientate the video signal in relation to the gravity vector.

15. A remote inspection device, comprising:
   a flexible cable having a proximal end and a distal end;
   a substantially cylindrical imager housing concentrically aligned with and coupled to a distal end of the flexible cable;
   an imaging device embedded in the imager housing and operable to capture an image of a viewing area proximate to the distal end of the flexible cable and convert the image into a video signal;
   two light sources protruding from the outwardly facing end of the cylindrical imager housing and disposed along a perimeter of the imaging device which is recessed between the light sources;
   a transparent cap attached to the outwardly facing end of the imager housing to encase the imaging device and the light sources, each of the light sources protrudes into a nipple that is formed in the car and configured to focus light from the light source into the viewing area;
   a display housing detachably coupled via a coupling to the proximate end of the flexible cable and configured to be grasped by a user of the device, wherein the display housing includes a display device adapted to receive the video signal from the imaging device and operable to convert the video signal into an image;
   a portable power source located in the display housing for providing electrical power to the device; and
   a plurality of wires located in the flexible cable to provide electrical power from the portable power source to the imaging device and the light source, and transmit the video signal from the imaging device to the display device.

16. The inspection device of claim 15 wherein the cylindrical imager housing detachably couples via a coupling to the distal end of the flexible cable and further comprises a cylindrical sleeve slidably attached to the distal end of the flexible cable, wherein the coupling between the imager housing and the flexible cable is formed by a threaded portion along an exterior surface of a cylindrical sleeve protruding from the imager housing and a grooved portion formed along an interior surface of the cylindrical coupling.

17. The inspection device of claim 16 wherein the coupling further includes an electrical connector disposed in an axial passageway of the cylindrical sleeve and another electrical connector disposed at the distal end of the flexible cable, wherein the electrical connects mate to form an electrical connection between the imager housing and the flexible cable.

18. The inspection device of claim 15 wherein the cylindrical imager housing detachably couples via a coupling to the distal end of the flexible cable and further comprises a cylindrical sleeve slidably attached to the proximate end of the flexible cable, wherein the coupling between the display housing and the flexible cable is formed by a threaded portion along an exterior surface of a cylindrical sleeve protruding from the display housing and a grooved portion formed along an interior surface of the cylindrical coupling.

19. The inspection device of claim 18 wherein the coupling further includes an electrical connector disposed in an axial passageway of the cylindrical sleeve and another electrical connector disposed at the proximate end of the flexible cable, wherein the electrical connects mate to form an electrical connection between the display housing and the flexible cable.

20. The remote inspection device of claim 15 wherein the light sources are further defined as light emitting diodes.

21. The remote inspection device of claim 20 wherein the cap is made of a transparent plastic.

22. The remote inspection device of claim 21 wherein the cap is ultrasonic welded to the imager housing.

23. The remote inspection device of claim 22 wherein the housing display having a shape of a pistol.

24. The remote inspection device of claim 23 wherein the housing display having a handle portion configured to be grasped by a user of the device and a protruding portion extending away from the user when grasped by the user, such that the protruding portion form an obtuse angle relative to the handle portion of the housing display.

* * * * *

UNITED STATES PATENT AND TRADEMARK OFFICE
CERTIFICATE OF CORRECTION

| | | |
|---|---|---|
| PATENT NO. | : 7,584,534 B2 | Page 1 of 1 |
| APPLICATION NO. | : 11/480329 | |
| DATED | : September 8, 2009 | |
| INVENTOR(S) | : Alfred A. Pease et al. | |

It is certified that error appears in the above-identified patent and that said Letters Patent is hereby corrected as shown below:

<u>Title Page</u>, Item [56] References Cited,
U.S. PATENT DOCUMENTS, insert -- 2005/0049461   3/2005   Honda et al --.
FOREIGN PATENT DOCUMENTS, "WO2006/075650", "11/2007" should be
-- 07/2006 --.

Item [57] ABSTRACT, line 3, "a" (first occurrence) should be -- an --.

<u>Column 8</u>,
Line 53, "car" should be -- cap --.

<u>Column 9</u>,
Line 15, "connects" should be -- connectors --.

<u>Column 10</u>,
Line 7, "connects" should be -- connectors --.

Signed and Sealed this

Tenth Day of November, 2009

David J. Kappos
*Director of the United States Patent and Trademark Office*